United States Patent [19]
Togo et al.

[11] 4,036,861
[45] July 19, 1977

[54] PROCESS FOR PRODUCING A 2-TERTIARY-ALKYL SUBSTITUTED ANTHRAQUINONE

[75] Inventors: Shizuo Togo; Muneo Ito; Chiharu Nishizawa; Michio Ohba, all of Tokyo, Japan

[73] Assignee: Mitsubishi Gas Chemical Company, Inc., Tokyo, Japan

[21] Appl. No.: 696,835

[22] Filed: June 17, 1976

[30] Foreign Application Priority Data

June 25, 1975 Japan .................................. 50-79281

[51] Int. Cl.² .............................................. C09B 1/00
[52] U.S. Cl. ............................................... 260/369
[58] Field of Search ....................................... 260/369

[56] References Cited
FOREIGN PATENT DOCUMENTS 2,050,798   4/1972   Germany ............................. 260/396

*Primary Examiner*—Paul F. Shaver
*Attorney, Agent, or Firm*—Flynn & Frishauf

[57] ABSTRACT

A process for producing a 2-tertiary-alkyl substituted anthraquinone, characterized by carrying out catalytic oxidation of a diphenylmethane type compound having the formula

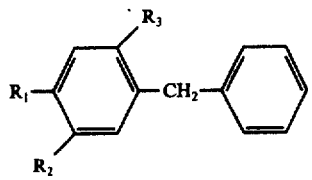

wherein $R_1$ and $R_2$ are different from each other, and independently hydrogen or tertiary-alkyl having 4 and 5 carbon atoms with the proviso that one of $R_1$ and $R_2$ is hydrogen, and $R_3$ is alkyl having 1-3 carbon atoms, in vapor phase in the presence of a catalyst comprising vanadium oxide is disclosed.

10 Claims, No Drawings

PROCESS FOR PRODUCING A 2-TERTIARY-ALKYL SUBSTITUTED ANTHRAQUINONE

BACKGROUND OF THE INVENTION

This invention relates to a process for producing a 2-tertiary-alkyl substituted anthraquinone, and particularly relates to a process for producing a 2-tertiary-alkyl substituted anthraquinone, characterized by carrying out catalytic oxidation of a diphenylmethane type compound having the formula

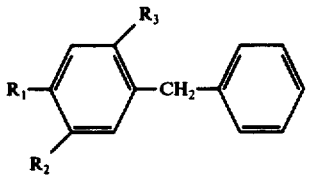

wherein $R_1$ and $R_2$ are different from each other, and independently hydrogen or tertiary-alkyl having 4 and 5 carbon atoms with the proviso that one of $R_1$ and $R_2$ is hydrogen, and $R_3$ is alkyl having 1–3 carbon atoms, in vapor phase in the presence of a catalyst comprising vanadium oxide.

In the prior art, a process for producing an alkyl substituted anthraquinone which comprises reacting phthalic anhydride with an alkyl benzene in the presence of a Friedel-Crafts catalyst was known. In this process, the operation is complicated. In addition, since a large amount of aluminum chloride and a large amount of concentrated sulfuric acid are necessary in this process, disposal of the wastes from the reaction is difficult. Furthermore, since isomerization reaction, rearrangement reaction and elimination reaction of the alkyl group occur in the above process, many by-products derived from these reactions contaminate the object product.

The processes for producing a non-substituted anthraquinone are disclosed in Japanese Publication (first) Nos. 47-576; 48-61463 and 49-75568. These processes comprise carrying out catalytic oxidation of indanes, such as 1-methyl-3-phenyl indane, or diphenylmethanes, such as o-benzyltoluene, in vapor phase. However, we have found that when catalytic oxidation of o-benzyltoluene was carried out in vapor phase, a large amount of p-benzylbenzaldehyde was formed as a by-product, and therefore, the yield of anthraquinone was as low as from 40 to 45%. We have also found that when catalytic oxidation of o-benzyltoluene substituted by an alkyl group, such as methyl, ethyl or propyl, was carried out in vapor phase, the oxidation of the alkyl group substituted on the benzene nucleus occurred, and therefore, the yield of alkyl substituted anthraquinone was decreased.

SUMMARY OF THE INVENTION

We have found that when a diphenylmethane type compound in which one of the benzene nuclei is substituted with two alkyl groups including a tertiary-alkyl group, represented by the formula

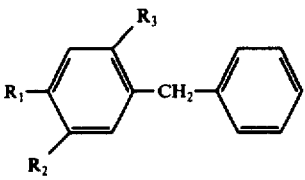

wherein $R_1$ and $R_2$ are different from each other, and independently hydrogen or tertiary-alkyl having 4 and 5 carbon atoms with the proviso that one of $R_1$ and $R_2$ is hydrogen, and $R_3$ is alkyl having 1–3 carbon atoms, was subjected to catalytic vapor phase oxidation in the presence of a catalyst comprising vanadium oxide, a 2-tertiary-alkyl substituted anthraquinone could be obtained in a high yield with little or no formation of a benzylbenzaldehyde type compound. The tert-alkyl group on the diphenylmethane type compound is not subjected to oxidation during the oxidation reaction and rather promotes conversion of the compound to the anthraquinone. This invention is formed on the basis of this discovery.

Therefore, one object of this invention is to provide a process for producing a 2-tert-alkyl substituted anthraquinone in which disposal of wastes is unnecessary.

Another object of this invention is to provide a process for producing a 2-tert-alkyl substituted anthraquinone with little or no formation of by-products.

DETAILED DESCRIPTION OF THE INVENTION

The 2-tert-alkyl substituted anthraquinone obtained according to the present invention is useful as a working material for the preparation of hydrogen peroxide by the anthraquinone method, as a dyestuff intermediate and as a raw material for organic synthesis.

Typical examples of the diphenylmethane type compound having the formula I include 4tert-butyl-2-benzyltoluene, 5-tert-butyl-2-benzyltoluene, 4-tert-amyl-2-benzyltoluene, 5-tert-amyl-2-benzyltoluene, 4-tert-butyl-2-benzylethylbenzene, 5tert-butyl-2-benzylethylbenzene, 4-tert-amyl-2benzylethylbenzene, 5-tert-amyl-2benzylethylbenzene, 4-tert-butyl-2-benzylcumene, 5-tert-butyl-2-benzylcumene, 4-tert-amyl-2-benzylcumene, 5-tert-amyl-2-benzylcumene and the like. 4-tertiary-butyl-2-benzyltoluene, 4-tertiary-amyl-2-benzyltoluene, 5-tertiary-butyl-2-benzyltoluene and 5-tertiary-amyl-2-benzyltoluene are preferred.

It is critical that two alkyl groups including one tert-alkyl is present on one benzene nucleus of the diphenylmethane type compound. As shown in the following Comparative Examples, we found that when catalytic oxidation of a diphenylmethane type compound, in which one alkyl group was present on one benzene nucleus of the compound, whereas the other alkyl group was present on the other benzene nucleus of the compound, was carried out in vapor phase, a 2-tert-alkyl substituted anthraquinone could not be obtained in a high yield because of formation of a considerable amount of a by-product, namely 2-(4′-tert-alkylbenzyl)-benzaldehyde.

In the practice of this invention, it is critical that the catalyst for oxidizing the diphenylmethane type compound in vapor phase contains vanadium oxide.

The catalyst may consist essentially of vanadium oxide, such as vanadium pentoxide. Advantageously, the catalyst may comprise vanadium pentoxide and other metal compound(s) for improving catalytic activity or selectivity. The other metal compounds which are usable with vanadium oxide include, for example, alkali metal compounds, thallium compounds, uranium compounds, titanium compounds, antimony compounds and the like. It is preferred that the other metal compound be in the form of an oxide. If necessary, two or more other metal compounds may be used with vanadium oxide. Combinations such as vanadium oxide-thallium oxide and vanadium oxide-uranium oxide are more preferred.

The vanadium oxide catalyst or the catalyst comprising vanadium oxide and the other metal compound(s) may be used in the form of particles per se. These catalysts may be conveniently used in the state in which they are carried on an inert carrier, such as on electrofused alumina, silicon carbide, spongy alumina and the like. An amount of the catalyst to be carried on the inert carrier is from about 1 to about 15% by weight based on the amount of the inert carrier.

The diphenylmethane type compound which is a starting material is subjected to gasification, and then the compound in a gaseous state is mixed with an oxidizing agent. The mixture of the compound and the oxidizing agent in gaseous state is passed through a reactor filled with the catalyst to oxidize the compound. The concentration of the diphenylmethane type compound having the formula I in the oxidizing agent is not critical. Advantageously, the concentration may range from about 0.1% by mol to about 0.6% by mol. The oxidizing agent means an oxygen-containing gas, and includes air or a mixture of oxygen and an inert gas. Air is preferred. The space velocity of the starting material-containing gas is not critical. In general, the space velocity may range from about 2,000 $Hr^{-1}$ to about 15,000 $Hr^{-1}$, preferably from about 2,000 $Hr^{-1}$ to about 7,000 $Hr^{-1}$.

The reaction temperature is not critical. The temperature may conveniently range from about 300° to about 550° C, preferably from about 350° to about 500° C.

In the practice of this invention, the mixture of the diphenylmethane type compound and the oxidizing agent may contain steam for increasing the yield of the anthraquinone. Steam may be incorporated in an amount of from 0.5 to 5% by volume based on the volume of the gaseous reactant containing the oxidizing agent.

The reaction of this invention may be effected under one atmospheric pressure, a superpressure or a reduced pressure.

After the catalytic oxidation of the compound is completed, the objective anthraquinone can be separated from the resulting mixed gas by a known process. For example, the objective anthraquinone can be separated from the mixed gas by condensing the gas or allowing the gas to be absorbed in an organic solvent, followed by distilling the object product or by crystallizing the object product.

Processes for producing the diphenylmethane type compound represented by the formula I are known. For example, one of the known processes is as follows:

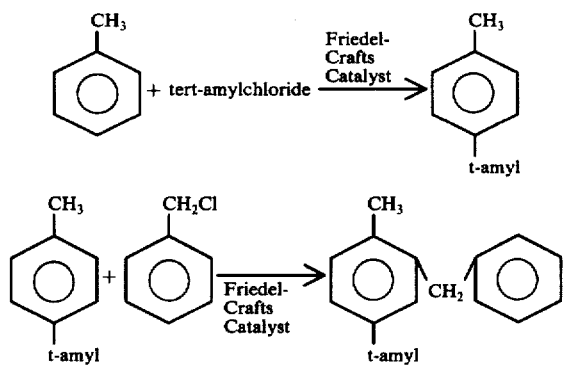

The diphenylmethane type compounds obtained by other methods are also usable as starting materials of this invention.

The present invention is further illustrated by the following Examples. However, this invention should not be limited by these examples, and changes and modification within the spirit and scope of this invention can be effected.

EXAMPLE 1

Preparation of 2-tert-butylanthraquinone

In a reactor 52 gr of ammonium metavanadate was suspended in 200 gr of water. To the resulting mixture was added 104 gr of oxalic acid dihydrate. The resulting mixture was heated to 80° C to obtain a blue solution. To the blue solution was added 400 gr of electrofused alumina (average diameter 3 mm). The solution was heated and dried on a water bath to obtain a catalyst carried on the alumina. The catalyst was pre-dryed at temperature of 180° C for 10 hours. A reactor made of stainless steel was filled with the predryed catalyst which was calcined at a temperature of 500° C for 3 hours while passing air therethrough.

The calcined catalyst was put in a reactor made of stainless steel. A mixture of 4-tert-butyl-2-benzyltoluene (90% by mole) and 5-tert-butyl-2-benzyltoluene (10% by mol) which was previously subjected to gasification and was mixed with air was subjected to catalytic oxidation by passing it through the catalyst bed under the following reaction conditions.

Reaction conditions:
Optimum reaction temperature — 385° C
Space velocity — 6000 $Hr^{-1}$
Concentration of starting material in air —0.2% by mol
Reaction results (measured by gas chromatography):
Conversion — 97.7%
Yield of 2-tert-butyl-anthraquinone — 50.6% by mol
Yield of 4-tert-butyl-2-benzylbenzaldehyde —trace The objective anthraquinone was separated from the reaction product by a crystallization procedure which comprised dissolving the crude reaction product in methanol and then cooling the methanol solution to crystallize the objective anthraquinone. The 2-tert-butylanthraquinone so obtained has a melting point of 102.5°– 103° C.

Elementary analysis: Found: C,81.0%; H,5.7 %. Calculated: C,81.8%; H,6.1%.

EXAMPLE 2

Preparation of 2-tert-butylanthraquinone

In a reactor 12.3 gr of ammonium metavanadate was suspended in 150 ml of water. To the resulting mixture was added 25 gr of oxalic acid dihydrate. The resulting mixture was heated to 80° C to obtain a blue solution. To the resulting solution were added 1.00 gr of titanium tetrachloride and 0.355 gr of cesium chloride. The resulting solution was thoroughly stirred. To the solution was added 100 gr of electrofused alumina (average diameter 3 mm). The solution was heated and dried on a water bath to obtain a catalyst carried on the alumina. The catalyst was predryed at temperature of 180° C for 10 hours. A reactor made of stainless steel was filled with the predryed catalyst which was calcined at temperature of 500° C for 3 hours while passing air therethrough. The atomic ratio of an effective components in the resulting catalyst was V:Ti:Cs = 100:5:2.

The catalytic oxidation was effected by using the above catalyst under the same reaction conditions as in Example 1. Analysis and separation of the reaction product were effected in the same procedure as in Example 1.

Reaction results:
Conversion — 99.4%
Optimum reaction temperature — 400° C
Yield of 2-tert-butylanthraquinone — 60.1% by mol
Yield of 4-tert-butyl-benzylbenzaldehyde — trace

COMPARATIVE EXAMPLE 1

The procedure of Example 1 was repeated except that the catalyst obtained in Example 2 and o-benzyltoluene as a starting material was used. The results are shown in Table 1. Anthraquinone so obtained had a melting point Table 1

| Reaction Temperature (° C) | Concentration of o-benzyltoluene (% by mol) | SV (Hr$^{-1}$) | Conversion of o-benzyltoluene (%)* | Yield of anthraquinone (% by mol)* | Yield of o-benzylbenzaldehyde (% by mol)* |
| --- | --- | --- | --- | --- | --- |
| 410 | 0.28 | 6000 | 91.0 | 37.6 | 21.7 |
| 422 | 0.28 | 6000 | 97.5 | 37.3 | 19.6 |
| 430 (optimum reaction temperature) | 0.28 | 6000 | 100.0 | 45.0 | 16.4 |

*measured by gas chromatography of 283 - 285° C. (286° C according to the chemical literature)

COMPARATIVE EXAMPLE 2

The procedure of Example 1 was repeated except that the catalyst obtained in Example 2 was used, that the starting material was 4-methyl-2-benzyltoluene diluted with air to 0.27% by mol and that space velocity was 6000 Hr$^{-1}$.

Reaction results:
Optimum reaction temperature — 406° C
Conversion — 77.4%
Yield of 2-methylanthraquinone — 6.1% by mol The main product so obtained was a material in tar state.

EXAMPLE 3

The procedure of Example 1 was repeated except that the catalyst obtained in Example 2 was used, that the starting material was 4-tert-butyl-2-benzylethylbenzene (concentration : 0.2 mol%) and the space velocity was 6000 Hr$^{-1}$.

Reaction results: (measured by gas chromatography)
Optimum reaction temperature 400° C
Conversion 100%
Yield of 2-tert-butylanthraquinone 52.6% by mol The separation of the reaction product was effected by the same procedure as in Example 1.

EXAMPLE 4

The procedure of Example 3 was repeated except that the mixture of 4-tert-amyl-2-benzyltoluene (90 mol%) and 5-tert-amyl-2-benzyltoluene (10 mol%) was used in place of 4-tert-butyl-2-benzylethylbenzene. The results measured by gas chromatography are as follows:
Optimum reaction temperature — 400° C
Conversion — 97.3%
Yield of 2-tert-amylanthraquinone — 45.0% (by mol)
Yield of 4-tert-2-benzylbenzaldehyde — 1.8% (by mol)

The separation procedure of the reaction product was the same as in Example 1, and 2-tert-amylanthraquinone so obtained has a melting point of 77° - 78° C.

Elementary analysis: Found: C,81.6%; H,6.4%. Calculated: C,82.0%, H,6.5%.

COMPARATIVE EXAMPLE 3

The procedure of Example 1 was repeated except that the catalyst obtained in Example 2 was used, that the starting material was 2-(4'-tert-amylbenzyl)toluene diluted with air to 0.2% by mol and that space velocity was 6000 Hr$^{-1}$. The results measured by gas chromatography are as follows:
Optimum reaction temperature — 404° C
Conversion — 97.7%
Yield of 2-tert-amylanthraquinone — 34.8% (by mol)
Yield of 2-(4'-amylbenzyl)benzaldehyde — 13.9% (by mol)

EXAMPLE 5-9 AND COMPARATIVE EXAMPLE 4

The catalysts shown in Table 2 were prepared in the same way as in Example 1 or Example 2. The catalytic oxidation was effected by using the catalyst and the starting material of Example 4 under the same reaction conditions as in Example 4. The results are shown in Table 2.

For comparison, the above procedure was repeated except that 2-(4'-tert-amylbenzyl)toluene was used as a starting material in place of 4-tert-amyl-2-benzyltoluene.

The results are in Table 2 as Comparative Example 4.

Table 2

| Example No. | Catalyst (atomic ratio) | Carrier | Optimum reaction temp. (° C) | Conversion (%)* | Yield of 2-tert-amyl-anthraquinone (% by mol)* | Yield of 4-tert-amyl-2-benzylbenzaldehyde (% by mol)* |
| --- | --- | --- | --- | --- | --- | --- |
| 5 | V$_2$O$_5$-CsCl | electrofused | 434 | 93.9 | 44.9 | 1.0 |

Table 2-continued

| Example No. | Catalyst (atomic ratio) | Carrier | Optimum reaction temp. (° C) | Conversion (%)* | Yield of 2-tert-amyl-anthraquinone (% by mol)* | Yield of 4-tert-amyl-2-benzylbenz-aldehyde (% by mol)* |
|---|---|---|---|---|---|---|
| 6 | $V_2O_5$-$TiO_2$-$K_2SO_4$-$Na_2SO_4$ (100:5:2.5:1.5) | alumina electrofused alumina | 381 | 96.5 | 39.5 | 1.5 |
| 7 | $V_2O_5$-$KH_2PO_4$ (100:7) | silicon carbide | 430 | 94.1 | 41.0 | 1.4 |
| 8 | $V_2O_5$-$Tl_2O_3$ (100:6) | spongy aluminum | 390 | 96.9 | 53.7 | 1.0 |
| 9 | $V_2O_5$-$UO_3$ (100:20) | spongy aluminum | 398 | 100.0 | 55.0 | 0.7 |
| Comparative Example 4 | $V_2O_5$-$TiO_2$-$K_2SO_4$-$Na_2SO_4$ (100:5:2.5:1.5) | electrofused alumina | 403 | 96.4 | 31.0 | Yield of 2-(4'-tert-amyl-benzyl)-benzaldehyde 9.3* |

*measured by gas chromatography

EXAMPLE 10

The procedure of Example 4 was repeated except that steam was incorporated in the feeding material consisting of the starting material and air. The results are shown in Table 3.

Table 3

| Ex. No. | Proportion of steam in feeding material (% by volume) | Conversion (%)* | Yield of 2-tert-amyl-anthraquinone (% by mol)* | Yield of 4-t-amyl-2-benzylbenz-aldehyde (% by mol)* |
|---|---|---|---|---|
| 4 | 0 | 97.3 | 45.0 | 1.8 |
| 10 | 2.2 | 98.8 | 50.1 | 1.7 |
|  | 4.4 | 98.9 | 46.1 | 1.7 |

*measured by gas chromatography

EXAMPLE 11

Preparation of 2-tert-amylanthraquinone

In a reactor 2.58 gr of ammonium metavanadate was suspended in 50 gr of water. To the resulting mixture was added 10 gr of oxalic acid dihydrate. The resulting mixture was heated to 80° C to obtain a blue solution. To the blue solution was added 1.88 g of uranyl acetate. The resulting solution was sprayed on 100 gr of heating spongy aluminum (average diameter 3mm). Then the resulting mixture was heated and dried on a water bath to obtain catalyst carried on the spongy aluminum. The catalyst was predryed at temperature of 180° C for 10 hours. The predryed catalyst was filled in a reactor made of a stainless steel and was calcined at temperature of 500° C for 3hours while passing air therethrough. The atomic ratio in the resulting catalyst was V:U = 100:20.

The calcined catalyst was filled in a reactor made of a stainless steel. The mixture of 4-tert-amyl-2-benzyl-toluene (90% by mole) and 4-tert-amyl-2-benzyltoluene (10% by mol) which was previously subjected to gasification and was mixed with air, was subjected to catalytic oxidation by passing it through the catalyst bed under the following reaction conditions.

Reaction conditions:
Optimum reaction temperature — 403° C
Space velocity — 3000 $Hr^{-1}$
Concentration of starting material in air — 0.2% by mol
Reaction results (measured by gas chromatography):
Conversion — 100.0%
Yield of 2-tert-amyl-anthraquinone — 60.6% by mol
Yield of 4-tert-amyl-2-benzylbenzaldehyde — 1.1% by mol The separation of the reaction product was effected in the same procedure as in Example 1.

EXAMPLE 12

In the preparation of the catalyst the procedure of Example 11 was repeated except that 0.35 g of thallous acetate was used in place of 1.88 g of uranyl acetate. The atomic ratio in the resulting catalyst was V:Tl = 100:6.

The same raw material and oxidation procedure as in Example 11 were effected in this Example. Reaction conditions and reaction results measured by gas chromatography are as follows:

Reaction conditions:
Optimum reaction temperature — 395° C
Space velocity — 3000 $Hr^{-1}$
Concentration of starting material in air — 0.2% by mol
Reaction results:
Conversion — 97.2%
Yield of 2-tert-amyl-anthraquinone — 55.0% by mol
Yield of 4-tert-amyl-2-benzylbenzaldehyde — 1.5% by mol

What we claim is:

1. A process for producing a 2-tertiary-alkyl substituted anthraquinone, characterised by carrying out catalytic oxidation of a diphenylmethane compound having the formula

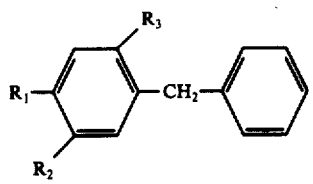

I wherein $R_1$ and $R_2$ are different from each other, and independently hydrogen or tertiary-alkyl having 4 and 5 carbon atoms with the proviso that one of $R_1$ and $R_2$ is hydrogen, and $R_3$ is alkyl having 1 - 3 carbon atoms, in vapor phase in the presence of a catalyst comprising vanadium oxide.

2. The process defined in claim 1, wherein the diphenylmethane compound is selected from the group consisting of 4-tertiary-butyl-2-benzyltoluene, 4-tertiaryamyl-2-benzyltoluene, 5-tertiary-butyl-2-benzyltoluene and 5-tertiary-amyl-2-benzyltoluene.

3. The process defined in claim 1, wherein the catalyst is composed of vanadium pentoxide.

4. The process defined in claim 1, wherein the catalyst is composed of a mixture of vanadium pentoxide and one or more other metal compounds.

5. The process defined in claim 4, wherein said one or more other metal compounds are selected from the group consisting of an alkali metal compound, a thallium compound, an uranium compound, a titanium compound, an antimony compound and mixture thereof.

6. The process defined in claim 4, wherein the catalyst is in combination of vanadium oxide with one member selected from the group consisting of uranium oxide and thallium oxide.

7. The process defined in claim 1, wherein the catalyst is carried on a carrier selected from the group consisting of electrofused alumina, silicon carbide and spongy aluminum.

8. The process defined in claim 1, wherein the catalytic oxidation is effected by passing the mixture of the diphenylmethane compound and an oxidizing agent in a gaseous state through a reactor filled with the catalyst.

9. The process defined in claim 8, wherein the oxidizing agent is air.

10. The process defined in claim 8, wherein the proportion of the diphenylmethane type compound in the mixture ranges from about 0.1% by mol to about 0.6% by mol.

* * * * *